United States Patent [19]
Hillman et al.

[11] Patent Number: 6,013,450
[45] Date of Patent: Jan. 11, 2000

[54] CAF1-RELATED PROTEIN

[75] Inventors: Jennifer L. Hillman; Neil C. Corley, both of Mountain View; Henry Yue, Sunnyvale, all of Calif.

[73] Assignee: Incyte Pharmaceuticals, Inc., Palo Alto, Calif.

[21] Appl. No.: 09/027,137

[22] Filed: Feb. 20, 1998

[51] Int. Cl.$^7$ .............................. C12Q 1/68; C12P 21/02; C12N 15/12; C12N 15/63

[52] U.S. Cl. .......................... 435/6; 435/69.1; 435/252.3; 435/320.1; 536/23.5; 536/24.31

[58] Field of Search .......................... 435/6, 69.1, 252.3, 435/320.1, 325; 536/23.1, 23.5, 24.3, 24.31, 24.33

[56] References Cited

PUBLICATIONS

Stryer, L., *Biochemistry*, W.H. Freeman and Company, New York, pp. 998–999 (1995).

Denis, C.L. and T. Malvar, "The CCR4 Gene From *Saccharomyces cerevisiae* Is Required for Both Nonfermentative and spt–Mediated Gene Expression", *Genetics*, 124: 283–291 (1990).

Malvar, T. et al., "The CCR4 Protein From *Saccharomyces cerevisiae* Contains a Leucine–Rich Repeat Region Which is Required for Its Control of ADH2 Gene Expression", *Genetics*, 132: 951–962 (1992).

Draper, M.P. et al., "CCR4 Is a Glucose–Regulated Transcription Factor Whose Leucine–Rich Repeat Binds Several Proteins Important for Placing CCR4 in Its Proper Promoter Context", *Mol. Cell. Biol.*, 14: 4522–4531 (1994).

Draper, M.P. et al., "Identification of a Mouse Protein Whose Homolog in *Saccharomyces cerevisiae* Is a Component of the CCR4 Transctiptional Regulatory Complex", *Mol. Cell Biol.*, 15: 3487–3495 (1995).

Sakai, A., "Molecular analysis of POP2 gene, a gene required for glucose–derepession of gene expression in *Saccharomyces cerevisiae*", *Nuc. Acids Res.*, 20: 6227–6233 (1992).

Liu, H.Y. et al., "DBF2, a cell cycle–regulated protein kinase, is physically and functionally associated with the CCR4 transcriptional regulatory complex", *EMBO J.*, 16: 5289–5298 (1997).

Latchman, D., *Gene Regulation*, Chapman and Hall, London, UK, pp. 242–255 (1995).

Draper, M.P. et al., (Direct Submission), GenBank Sequence Database (Accession 726136), National Center for Biotechnology Information, National Library of Medicine, Bethesda, Maryland, 20894, (GI 726136) Feb. 12, 1996.

Draper, M.P. et al., (Direct Submission), GenBank Sequence Database (Accession U21855), National Center for Biotechnology Information, National Library of Medicine, Bethesda, Maryland, 20894, (GI 726135; GI 726136) Feb. 14, 1996.

Hillier et al. (Sep. 30, 1997) GenBank, EST clone 743401. Accession No. AA609336. Accessed May 14, 1998, Sep. 1997.

*Primary Examiner*—George C. Elliott
*Assistant Examiner*—Robert Schwartzman
*Attorney, Agent, or Firm*—Incyte Pharmaceuticals, Inc.

[57] ABSTRACT

The invention provides a human CAF1-related protein (CAFRP) and polynucleotides which identify and encode CAFRP. The invention also provides expression vectors, host cells, antibodies, agonists, and antagonists. The invention also provides methods for treating or preventing disorders associated with expression of CAFRP.

11 Claims, 10 Drawing Sheets

```
5'-CC GTG GGA GGC ACG TAA GAC CGC TCT GGG CAC GGG GCT CAC CTC ACT GGC
                 9      18          27          36          45      54

TCG TTC GGT TCT AGG AGC AGA TCC GGG GTA GAG GGA AAA GAG CTC CGG GCC AGG
         63          72          81          90          99         108

GGC TGC CGT CGC CGC CGT CGG GGA GTC AGC CCG GCC CCA GCC CGC CAG CTC AGC
        117         126         135         144         153         162

CCG CCA GCC AGC GCT TCG CGG GCC CTG TCG GTC CCG ATC AGA CCA AAC ATT GTC
        171         180         189         198         207         216

TGG CTT GCA CTG TAA AAC TAG TTA GCT GAA GAC TTC TCA GGT TTC TTC AGG
        225         234         243         252         261         270

ATG CCT GCA GCA CTT GTG GAG AAT AGC CAG GTT ATC TGT GAA GTG TGG GCC AGT
 M   P   A   A   L   V   E   N   S   Q   V   I   C   E   V   W   A   S
        279         288         297         306         315         324

ATG GAA GAA GAG ATG AGG AAG ATC CGA GAA ATC GTG CTC AGT TAC AGT TAT
 M   E   E   E   M   R   K   I   R   E   I   V   L   S   Y   S   Y
        333         342         351         360         369         378

AAT CTA
 N   L
```

```
     387        396        405        414        423        432
ATT  ATG  GAC  ACA  GAA  TTT  CCA  GGT  GTG  GTT  CGA  CCA  ATT  GGT  GAA  TTT
 I    M    D    T    E    F    P    G    V    V    R    P    I    G    E    F 441        450        459        468        477        486
CGT  AGT  ATA  GAT  TAC  CAA  CTG  CAG  CTT  CTG  CGG  TGC  AAT  GTT  GAC  CTT  TTA
 R    S    I    D    Y    Q    L    Q    L    L    R    C    N    V    D    L    L 495        504        513        522        531        540
AAA  ATT  CAG  CTG  GGC  CTT  ACA  TTC  ACA  AAT  GAG  AAG  GGA  TAT  GAG  TAT  CCT  TCT
 K    I    Q    L    G    L    T    F    T    N    E    K    G    Y    E    Y    P    S 549        558        567        576        585        594
GGA  ATC  AAT  ACT  TGG  CAG  TTC  AAT  AAC  CTT  ACA  CTA  CAG  GAC  ATG  TAC
 G    I    N    T    W    Q    F    N    N    L    T    L    Q    D    M    Y 603        612        621        630        639        648
TCC  CAG  GAT  TCC  ATA  GAT  CTC  CTT  GCT  AAC  TCA  GGA  CTA  CAG  AAG  CAT
 S    Q    D    S    I    D    L    L    A    N    S    G    L    Q    K    H 657        666        675        684        693        702
GAA  GAG  GGG  ATT  GAC  ACA  CTG  CAC  TTT  GCA  GAG  CTG  CTT  ATG  ACA  TCA  AAG  GGA
 E    E    G    I    D    T    L    H    F    A    E    L    L    M    T    S    K    G 711        720        729        738        747        756
GTG  GTT  CTC  TGT  GAC  AAT  GTC  AAA  TGG  CTT  TCA  TTT  CAT  AGT  GGC  TAT  GAT  TTT
 V    V    L    C    D    N    V    K    W    L    S    F    H    S    G    Y    D    F
```

```
      765            774            783            792            801            810
GGC TAT ATG GTA AAG TTG CTT ACA GAT TCT CGT TTG CCA GAA GAG GAA CAT GAA
 G   Y   M   V   K   L   L   T   D   S   R   L   P   E   E   E   H   E 819            828            837            846            855            864
TTC TTT CAT ATT CTG AAC CTT TTC CCA TCC ATT TAT GAT GTG AAA TAC CTG
 F   F   H   I   L   N   L   F   P   S   I   Y   D   V   K   Y   L 873            882            891            900            909            918
ATG AAG AGC TGC AAA AAT CTT AAG GGA GGT CTT CAG GAA GTT GCT GAT CAG TTG
 M   K   S   C   K   N   L   K   G   G   L   Q   E   V   A   D   Q   L 927            936            945            954            963            972
GAT TTG CAG AGG ATT GGA AGG CAG AGG CAC CAG GCA GGC TCA GAC CTG CTG ACA
 D   L   Q   R   I   G   R   Q   R   H   Q   A   G   S   D   L   L   T 981            990            999           1008           1017           1026
GGA ATG GCT TTC TTT TTT GGG CGG ATG AAA GAG TTG TTT GAG GAC AGC ATT GAT GAT
 G   M   A   F   F   F   G   R   M   K   E   L   F   E   D   S   I   D   D 1035           1044           1053           1062           1071           1080
GCC AAG TAC TGT GGG CGG CTC TAT GGC TTA GGC ACA GGA GTG GCC CAG AAG CAG
 A   K   Y   C   G   R   L   Y   G   L   G   T   G   V   A   Q   K   Q 1089           1098           1107           1116           1125           1134
AAT GAG GAT GTG GAC TCT GCC CAG GAG AAG ATG AGC ATC CTG GCG ATT ATC AAC
 N   E   D   V   D   S   A   Q   E   K   M   S   I   L   A   I   I   N
```

FIGURE 1C

```
           1143           1152           1161           1170           1179           1188
AAC ATG CAG CAG TGA CAG TGG CGC CAG GCT CTG CAG GGT GGG CCT GAT CCC AGA GTG
 N   M   Q   Q
           1197           1206           1215           1224           1233           1242
GTG CTT ACT GTG CTG ACT GTG TAC TTA TCT TCC CCA AGA GAA AAT GCT TCT TTT
           1251           1260           1269           1278           1287           1296
GAG CAC ACT GTA CCT ACC ATC TGC ATT GAG CAG AAA GAC TTT TGT TTT ACT GAA
           1305           1314           1323           1332           1341           1350
GAC AAA AGA TGT TTT AGA CCC AGA AGA GAG TTT GCT CTG AAT TTG
           1359           1368           1377           1386           1395           1404
TAA ATA AGT CTT CCC CAT TCC TCA TAC TCG AGC CTC TCC TCT CTG GTT GCC TCC
           1413           1422           1431           1440           1449           1458
TGC CAC CAG CAT CCA TGG CTC ATT TGA CAC CTT TTT AAA TAT CAG GAC AAG TCT
           1467           1476           1485           1494           1503           1512
GAA ACA AAG TAG TAA AAT GTA TAT AAC TCT TAC CTG TTG TCA TTC TTT TTC TTT
```

FIGURE 1D

```
     1521        1530         1539        1548         1557        1566
TAA ATT TGT TGC TAA TCT CTG ATA ATG AAG ATT CTT ACT CTG ATT CTC AGC TGA 1575        1584         1593        1602         1611        1620
GCT GTG AGG GCT TCC AGG GAA AAT GGA ACA AAA TGG TGT TCT TAG GTA ATG GGT 1629        1638         1647        1656         1665        1674
TGT AGA TAC TGA GTC TTC CTT TCT GAC CCT TCT CGA GGA CAT TTG CTT 1683        1692         1701        1710         1719        1728
TCC TCA CAC TTT TGT AGT CTC TCT TTA CAT ATT ACT ATA TGG AAA TGA ATT GCT 1737        1746         1755        1764         1773        1782
CTG TGC TGA AAT TTG AAG ACC AGA TAA TGA AAC TGA AAA GCA AAC AAT TTT ACT 1791        1800         1809        1818         1827        1836
GAA TCT GTC TAC CCT TCA TTC ATG AGA ACT CCA GAA TGA GTG TTG ACC ACT GAA 1845        1854         1863        1872         1881        1890
GCA TCT TTT AAG TCT GTG TTC CAT TGT GCC ATT CAG GTT TGC TGT CAC ATA TGC
```

FIGURE 1E

```
           1899            1908           1917           1926           1935      1944
ATC ATC TGA AAT CAT TTG AAA TTT TTG TAC AAT AAA ATA TCC TGG ATT TGA TCC 1953            1962           1971           1980           1989      1998
TGA AGG AAA CTA GTA AGA TCA GAT TTT TGG GTC ATG TCT GTT GTA TTT TCA GTA 2007            2016           2025           2034           2043      2052
ATG TGA TTT CAG ATG GTC ATC TGG ATT CTC CCA CTT CTC TAC TCC ATT ATT TCT 2061            2070           2079           2088           2097      2106
CTA CTT TTC CTT CCA GCA AAC CTG AAA CGT GAG GGA GAT GGA TTA ATG TGA GTA 2115            2124           2133           2142           2151      2160
ACA GAA ATG TGT CTT TAA AAA GCT AGA GTG GTT ACA TTT AAT CAG GCA GTA AGA 2169            2178           2187           2196           2205      2214
TAA TTT GGG TTC TTG AGT TGT TTT GGA GTA ATA TCC CAC AAC TGG GGT AGG AAG 2223            2232           2241           2250           2259      2268
CTC AGG ACT TTT TTC TTT AAA GCT AGT CAT TTC AAA AGC ATA TTG TAT TTT TTT
```

FIGURE 1F

```
                 2277             2286             2295             2304             2313             2322
           GAA TGA CTA CAG TAT GGA CAA TTT CAA AAA CCA AAA CCC ACT TTG GAT TGG TGG 2331             2340             2349             2358             2367             2376
           AAG TAA AAA CTG GTA ACT CAC TCA AGT GAA TGA ATG GTC TTG CAT TTT AAA AGC 2385             2394             2403             2412             2421             2430
           TTA TGG GAA ACT CAA TTT GAA ATG ATT AGA AAA TGT CAA GTA TTA TAA GCT GGT 2439             2448             2457             2466             2475             2484
           ATT TAA GAT GCT TGT AAA TAC TAT TTA TGT TTT TAA TTT TGT AAA ATA AAG ATT 2493             2502             2511             2520             2529             2538
           TCT TTT TAA CCA CTG GCA AAA AAA AAA AAA AAA AAA AAA AAA AAA AAA AAA AAA 2547             2556             2565             2574             2583             2592
           AAA AAA AAA AAA AAA AAA AAA AAA AAA AAA AAA AAA AAA AAA AAA AAA AGG GGG 2601             2610             2619             2628             2637             2646
           GGC CGC TCT AGG GGT CCC AGG TTT AGG TAC GGG GGC TTG GGG GGT CAA GCC CCT
```

FIGURE 1G

```
              2655       2664            2673            2682            2691            2700
         CCT AAG GGG CCC CCA AAT TTC ATT TCC CGG GCG GCG GTT TTA AAA GGT CGT GCC 2709       2718            2727            2736            2745            2754
         GGG GAA ACC CCG GGG GTT CCC CAC TTT AAC CGC TTT GGG GAA ATC CCC CTT TTG 2763       2772            2781            2790            2799            2808
         GCA AGT GGG GGT ATT AGG GAA GGG GCC CGC CCG GTT GGC CTT TCC CAA AGT TTG 2817       2826            2835            2844            2853
         CGC CCT CTA ATT GGG CAT TGG GCC GCC CCC TTT AGG GGC GCT TTA 3'
```

CAF1-RELATED PROTEIN

FIELD OF THE INVENTION

This invention relates to nucleic acid and amino acid sequences of a CAF1-related protein and to the use of these sequences in the diagnosis, treatment, and prevention of disorders associated with cell proliferation and inflammation.

BACKGROUND OF THE INVENTION

Differential control of gene expression is essential to the growth and development of all multicellular organisms. Although gene expression can be controlled at many steps along the path from DNA to protein, the major control point for most genes is at the initiation of transcription. This critical step is regulated both positively and negatively by a combination of general and tissue specific transcription factors, the majority of which function to stimulate transcription of one or more target genes.

Many transcription factors are modular proteins that contain separable DNA binding and transcriptional activation (or repression) domains. The DNA binding domain interacts with specific DNA sequences (control elements) near the promoter region of the gene; this interaction brings the activation(or repression) domain into a position where it can interact with other proteins to stimulate (or repress) transcription. Many transcription factors require dimerization or multimerization to be fully functional. For example, members of the helix-loop-helix family of transcription factors function as homo-/or hetero-dimers. The monomeric forms of these factors lack DNA binding activity. (Stryer, L. (1995) Biochemistry, 4th ed., pp 998–999.)

CCR4 is a general transcription factor in yeast that appears to be a component of a multisubunit complex. CCR4 stimulates the expression of numerous genes involved in non-fermentative growth. In particular, CCR4 is required for expression of the glucose-repressible alcohol dehydrogenase II gene (ADH2). Although CCR4 does not appear to bind DNA directly, when fused to the DNA binding domain of LexA, CCR4 can function as a glucose responsive transcriptional activator. CCR4 physically interacts with several other protein factors. Two of these CCR4 associated factors, CAF1 and CAF2, bind to a leucine rich repeat motif in the middle of the CCR4 protein. (Denis, C. L. and Malvar, T. (1990) Genetics 124: 283–291; Malvar et al. (1992) Genetics 132 (4):951–962; Draper, M. P. et al. (1994) Mol. Cell. Biol. 14(7): 4522–4531; and Draper, M. P. et al. (1995) Mol. Cell. Biol. 15(7): 3487–3495.)

CAF1 is an evolutionarily conserved mouse protein, with homologs identified in human, S. cerevisiae, C. elegans, and A. thaliana. A yeast homolog of CAF1, POP2, was first identified by its effects on glucose regulated gene expression. Consistent with a proposed function as a transcription factor, both mouse CAF1 and yeast CAF1 can activate transcription of a LexA responsive reporter gene when fused to the LexA DNA binding domain. In addition, CAF1 contains several structural features commonly found in transcription factors, e.g., a proline-rich region, several glutamine-rich regions, and a serine/threonine-rich region. (Sakai, A. et al. (1992) Nuc. Acids Res. 20: 6227–6233; Draper, M. P. et al. (1995) supra.)

A second CCR4 associated factor, CAF2, is a yeast protein kinase that was first identified as DBF2 and shown to be required for cell cycle progression. Immunoprecipitation and yeast two hybrid studies demonstrated that CCR4, CAF1, and CAF2 associate in vivo to form a stable complex. In addition, mutations in the genes encoding CCR4, CAF1, or CAF2 result in a similar set of pleiotropic phenotypes, including specific transcriptional defects and cell cycle progression defects. For example, mutations in any of the three genes can suppress the elevated expression of the ADH2 and HIS4–912 genes that occurs in spt6 and spt10 mutants. Taken together, the results suggest that CAF1, CAF2, and CCR4 function together as components of an evolutionarily conserved multi-protein complex that regulates transcription of numerous genes. (Draper, M. P. et al. (1995) supra.; Liu, H. Y., et al. (1997) EMBO J. 16(17) :5289–5298.)

Defects in transcriptional regulation are known to contribute to oncogenesis, presumably through their affects on the expression of genes involved in cell proliferation. For example, mutant forms of transcription factors encoded by proto-oncogenes, e.g., Fos, Jun, Myc, Rel, and Spi1, may be oncogenic due to increased stimulation of cell proliferation. Conversely, mutant forms of transcription factors encoded by tumor suppressor genes, e.g., p53, RB1, and WT1, may be oncogenic due to decreased inhibition of cell proliferation. (Latchman, D. (1995) Gene Regulation: A Eukaryotic Perspective, 2nd ed. Chapman and Hall, London, UK, pp 242–255.)

The discovery of a new CAF1-related protein and the polynucleotides encoding it satisfies a need in the art by providing new compositions which are useful in the diagnosis, treatment, and prevention disorders associated with cell proliferation and inflammation.

SUMMARY OF THE INVENTION

The present invention is based upon the discovery of a new CAF1 related protein, herein after referred to as "CAFRP". The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide sequence identity to the polynucleotide encoding the polypeptide comprising the amino acid sequence of SEQ ID NO:1 or a fragment of SEQ ID NO:1.

Additionally, the invention provides a composition comprising a polynucleotide encoding the polypeptide comprising the amino acid sequence of SEQ ID NO:1 or a fragment of SEQ ID NO:1. The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention further provides a polynucleotide fragment useful for designing oligonucleotides or for use as a hybridization probe comprising nucleotides 1083 through 1113 of SEQ ID NO:1.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a disorder of cell proliferation, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing inflammation, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, 1F, 1G, and 1H show the amino acid sequence (SEQ ID NO:1) and nucleic acid sequence (SEQ ID NO:2) of CAF1-related protein. The alignment was produced using MACDNASIS PRO software (Hitachi Software Engineering Co. Ltd., San Bruno, Calif.).

FIGS. 2A and 2B show the amino acid sequence alignments between CAF1-related protein (Incyte Clone 2229466; SEQ ID NO:1), and mouse CAF1 protein (GI 726136; SEQ ID NO:3), produced using the multisequence alignment program of DNASTAR software (DNASTAR Inc, Madison, Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"CAFRP," as used herein, refers to the amino acid sequences of substantially purified CAFRP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to CAFRP, increases or prolongs the duration of the effect of CAFRP. Agonists may include proteins, nucleic acids, carbohydrates, or any other molecules which bind to and modulate the effect of CAFRP.

An "allele" or an "allelic sequence," as these terms are used herein, is an alternative form of the gene encoding CAFRP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding CAFRP, as described herein, include those sequences with deletions, insertions, or substitutions of different nucleotides, resulting in a polynucleotide the same CAFRP or a polypeptide with at least one functional characteristic of CAFRP. Included within this definition are polymorphisms which may or may not be readily detectable using a particular oligonucleotide probe of the polynucleotide encoding CAFRP, and improper or unexpected hybridization to alleles, with a locus other than the normal chromosomal locus for the polynucleotide sequence encoding CAFRP. The encoded protein may also be "altered," and may contain deletions, insertions, or substitutions of amino acid residues which produce a silent change and result in a functionally equivalent CAFRP. Deliberate amino acid substitutions may be made on the basis of similarity in polarity, charge, solubility, hydrophobicity, hydrophilicity, and/or the amphipathic nature of the residues, as long as the biological or immunological activity of CAFRP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of CAFRP which are preferably about 5 to about 15 amino acids in length and which retain some biological activity or immunological activity of CAFRP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp.1–5.)

The term "antagonist," as it is used herein, refers to a molecule which, when bound to CAFRP, decreases the amount or the duration of the effect of the biological or immunological activity of CAFRP. Antagonists may include proteins, nucleic acids, carbohydrates, antibodies, or any other molecules which decrease the effect of CAFRP.

As used herein, the term "antibody" refers to intact molecules as well as to fragments thereof, such as Fab, F(ab')$_2$, and Fv fragments, which are capable of binding the epitopic determinant. Antibodies that bind CAFRP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic CAFRP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding CAFRP or fragments of CAFRP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding CAFRP, by northern analysis is indicative of the presence of nucleic acids encoding CAFRP in a sample, and thereby correlates with expression of the transcript from the polynucleotide encoding CAFRP.

A "deletion," as the term is used herein, refers to a change in the amino acid or nucleotide sequence that results in the absence of one or more amino acid residues or nucleotides.

The term "derivative," as used herein, refers to the chemical modification of CAFRP, of a polynucleotide sequence encoding CAFRP, or of a polynucleotide sequence complementary to a polynucleotide sequence encoding CAFRP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison, Wis.). The MEGALIGN program can create alignments between two or more sequences according to different methods, e.g., the Clustal method. (See, e.g., Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides or oligonucleotides arrayed on a substrate, e.g., paper, nylon or any other type of membrane, filter, chip, glass slide, or any other suitable solid support.

The term "modulate," as it appears herein, refers to a change in the activity of CAFRP. For example, modulation may cause an increase or a decrease in protein activity, binding characteristics, or any other biological, functional, or immunological properties of CAFRP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.) The term "sample," as used herein, is used in its broadest sense. A biological sample suspected of containing nucleic acids encoding CAFRP, or fragments thereof, or CAFRP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of CAFRP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human CAF1-related protein (CAFRP), the polynucleotides encoding CAFRP, and the use of these compositions for the diagnosis, treatment, or prevention of disorders associated with cell proliferation and inflammation.

Nucleic acids encoding the CAFRP of the present invention were first identified in Incyte Clone 2229466 from the prostate cDNA library PROSNOT 16 using a computer search for amino acid sequence alignments. A consensus sequence, SEQ ID NO:2, was derived from the following overlapping and/or extended nucleic acid sequences: Incyte Clones 2743652 (BRSTTUT14), 2229466 (PROSNOT16), 2748488 (LUNGTUT11), 1443657 (THYRNOT03), 1714768 (UCMCNOT02), 1605302 (LUNGNOT15), 1697743 (BLADTUT05), and 725125 (SYNOOAT01).

In one embodiment, the invention encompasses a polypeptide comprising the amino acid sequence of SEQ ID NO:1, as shown in FIGS. 1A, 1B, 1C, 1D, 1E, 1F, 1G, and 1H. CAFRP is 292 amino acids in length and has a potential N-glycosylation site at residue $N_{102}$; six potential casein kinase II phosphorylation sites at residues $S_{18}$, $Sp_{56}$, $S_{158}$, $S_{191}$, $S_{249}$, and $S_{276}$; a potential protein kinase C (PKC) phosphorylation site at residue $S_{201}$ and a potential tyrosine phosphorylation site at residue $Y_{62}$. As shown in FIGS. 2A and 2B, CAFRP has chemical and structural homology with mouse CAF1 protein (GI 726136; SEQ ID NO:3). CAFRP and mouse CAF1 protein share 76% amino acid identity and are similar in their respective lengths (285 versus 292), isoelectric points (4.6 versus 4.7), and high content of leucine residues (11.6 versus 10.2%). Of particular note is the conservation of numerous sites for potential post-translational modifications, including the potential N glycosylation site at residue $N_{102}$, two potential casein kinase II phosphorylation site at $S_{56}$ and $S_{158}$; the potential PKC phosphorylation site at $S_{201}$; and the potential tyrosine phosphorylation site at residue $Y_{62}$. The fragment of SEQ ID NO:2 from about nucleotide 1083 to about nucleotide 1113 is useful as a hybridization probe. Northern analysis shows the expression CAFRP in various libraries, at least 48% of which are immortalized or cancerous, at least 27% of which involve immune response, and at least 14% involve fetal/proliferating cells. Of particular note is the widespread expression of CAFRP in libraries derived from reproductive, hematopoietic/immune, gastrointestinal, neural, and cardiovascular tissues.

The invention also encompasses CAFRP variants. A preferred CAFRP variant is one which has at least about 80%, more preferably at least about 90%, and most preferably at least about 95% amino acid sequence identity to the CAFRP amino acid sequence, and which contains at least one functional or structural characteristic of CAFRP.

The invention also encompasses polynucleotides which encode CAFRP. In a particular embodiment, the invention encompasses a polynucleotide sequence comprising the sequence of SEQ ID NO:2, which encodes a CAFRP.

The invention also encompasses a variant of a polynucleotide sequence encoding CAFRP. In particular, such a variant polynucleotide sequence will have at least about 80%, more preferably at least about 90%, and most preferably at least about 95% polynucleotide sequence identity to the polynucleotide sequence encoding CAFRP. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of CAFRP.

It will be appreciated by those skilled in the art that as a result of the degeneracy of the genetic code, a multitude of polynucleotide sequences encoding CAFRP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring CAFRP, and all such variations are to be considered as being specifically disclosed.

Although nucleotide sequences which encode CAFRP and its variants are preferably capable of hybridizing to the nucleotide sequence of the naturally occurring CAFRP under appropriately selected conditions of stringency, it may be advantageous to produce nucleotide sequences encoding CAFRP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CAFRP and its derivatives without altering the encoded amino acid sequences include the production of RNA transcripts having more desirable properties, such as a greater half-life, than transcripts produced from the naturally occurring sequence.

The invention also encompasses production of DNA sequences which encode CAFRP and CAFRP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding CAFRP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the MICRO LAB 2200 (Hamilton, Reno, Nev.), Peltier thermal cycler (PTC200; M J Research, Watertown, Mass.), and the ABI Catalyst and 373 and 377 DNA sequencers (Perkin Elmer).

The nucleic acid sequences encoding CAFRP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomnic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.)

Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR , Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode CAFRP may be used in recombinant DNA molecules to direct expression of CAFRP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express CAFRP.

As will be understood by those of skill in the art, it may be advantageous to produce CAFRP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter CAFRP-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding CAFRP may be ligated to a heterologous sequence to encode a fusion protein. For example, to screen peptide libraries for inhibitors of CAFRP activity, it may be useful to encode a chimeric CAFRP protein that can be recognized by a commercially available antibody. A fusion protein may also be engineered to contain a cleavage site located between the CAFRP encoding sequence and the heterologous protein sequence, so that CAFRP may be cleaved and purified away from the heterologous moiety.

In another embodiment, sequences encoding CAFRP may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, the protein itself may be produced using chemical methods to synthesize the amino acid sequence of CAFRP, or a fragment thereof. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer). Additionally, the amino acid sequence of CAFRP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties,* W H Freeman and Co., New York, N.Y.)

In order to express a biologically active CAFRP, the nucleotide sequences encoding CAFRP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding CAFRP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual,* Cold Spring Harbor Press, Plainview, N.Y., ch. 4, 8, and 16–17; and Ausubel, F. M. et al. (1995, and periodic supplements) *Current Protocols in Molecular Biology,* John Wiley & Sons, New York, N.Y., ch. 9, 13, and 16.)

A variety of expression vector/host systems may be utilized to contain and express sequences encoding CAFRP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding CAFRP which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla, Calif.) or PSPORT1 plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding CAFRP, vectors based on SV40 or EBV may be used with an appropriate selectable marker.

In bacterial systems, a number of expression vectors may be selected depending upon the use intended for CAFRP. For example, when large quantities of CAFRP are needed for the induction of antibodies, vectors which direct high level expression of fusion proteins that are readily purified may be used. Such vectors include, but are not limited to, multifunctional E. coli cloning and expression vectors such as BLUESCRIPT (Stratagene), in which the sequence encoding CAFRP may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae,* a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding CAFRP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express CAFRP. For example, in one such system, *Autographa californica* nuclear polyhedrosis virus (AcNPV) is used as a vector to express foreign genes in *Spodoptera frugiperda* cells or in Trichoplusia larvae. The sequences encoding CAFRP may be cloned into a non-essential region of the virus, such as the polyhedrin gene, and placed under control of the polyhedrin promoter. Successful insertion of sequences encoding CAFRP will render the polyhedrin gene inactive and produce recombinant virus lacking coat protein. The recombinant viruses may then be used to infect, for example, *S. frugiperda* cells or Trichoplusia larvae in which CAFRP may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding CAFRP may be ligated into an adenovirus transcription/translation complex consisting of the late promoter and tripartite leader sequence. Insertion in a non-essential E1 or E3 region of the viral genome may be used to obtain a viable virus which is capable of expressing CAFRP in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding CAFRP. Such signals include the ATG initiation codon and adjacent sequences. In cases where sequences encoding CAFRP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing CAFRP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk⁻ or apr⁻ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, B glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding CAFRP is inserted within a marker gene sequence, transformed cells containing sequences encoding CAFRP can be identified by the absence of marker gene function. Alternatively, a marker gene can be placed in tandem with a sequence encoding CAFRP under the control of a single promoter. Expression of the marker gene in response to induction or selection usually indicates expression of the tandem gene as well.

Alternatively, host cells which contain the nucleic acid sequence encoding CAFRP and express CAFRP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding CAFRP can be detected by DNA-DNA or DNA-RNA hybridization or amplification using probes or fragments or fragments of polynucleotides encoding CAFRP. Nucleic acid amplification based assays involve the use of oligonucleotides or oligomers based on the sequences encoding CAFRP to detect transformants containing DNA or RNA encoding CAFRP.

A variety of protocols for detecting and measuring the expression of CAFRP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on CAFRP is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding CAFRP include oligolabeling, nick translation, end-labeling, or PCR amplification using a labeled nucleotide. Alternatively, the sequences encoding CAFRP, or any fragments thereof, may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding CAFRP may be cultured under conditions suitable for the expression and recovery of the protein from cell culture. The protein produced by a transformed cell may be secreted or contained intracellularly depending on the sequence and/ or the vector used. As will be understood by those of skill in the art, expression vectors containing polynucleotides which encode CAFRP may be designed to contain signal sequences which direct secretion of CAFRP through a prokaryotic or eukaryotic cell membrane. Other constructions may be used to join sequences encoding CAFRP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the CAFRP encoding sequence may be used to facilitate purification. One such expression vector provides for expression of a fusion protein containing CAFRP and a nucleic acid encoding 6 histidine residues preceding a thioredoxin or an enterokinase cleavage site. The histidine residues facilitate purification on immobilized metal ion affinity chromatography (IMIAC). (See, e.g., Porath, J. et al. (1992) Prot. Exp. Purif. 3: 263–281.) The enterokinase cleavage site provides a means for purifying CAFRP from the fusion protein. (See, e.g., Kroll, D. J. et al. (1993) DNA Cell Biol. 12:441–453.)

Fragments of CAFRP may be produced not only by recombinant production, but also by direct peptide synthesis using solid-phase techniques. (See, e.g., Creighton, T. E. (1984) Protein: Structures and Molecular Properties, pp. 55–60, W. H. Freeman and Co., New York, N.Y.) Protein synthesis may be performed by manual techniques or by automation. Automated synthesis may be achieved, for example, using the Applied Biosystems 431A peptide synthesizer (Perkin Elmer). Various fragments of CAFRP may be synthesized separately and then combined to produce the full length molecule.

Therapeutics

Chemical and structural homology exists among CAFRP, CAF1 protein from mouse (GI726136) and POP2 protein from *S. cerevisiae* (GI218463). In addition, CAFRP is expressed in libraries derived from cancerous, inflamed, and proliferating cells and tissues. Therefore, CAFRP appears to play a role in disorders associated with cell proliferation and inflammation.

Therefore, in one embodiment, an antagonist of CAFRP may be administered to a subject to treat or prevent a disorder associated with cell proliferation. Such a disorder may include, but is not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding CAFRP may be administered to a subject to treat or prevent a disorder associated with cell proliferation, including, but not limited to, those described above.

In an additional embodiment, an antagonist of CAFRP may be administered to a subject to treat or prevent a disorder associated with inflammation. Such a disorder may include, but is not limited to AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In an additional embodiment, a vector expressing the complement of the polynucleotide encoding CAFRP may be administered to a subject to treat or prevent a disorder associated with inflammation, including, but not limited to, those described above.

In one aspect, an antibody which specifically binds CAFRP may be used directly as an antagonist or indirectly as a targeting or delivery mechanism for bringing a pharmaceutical agent to cells or tissue which express CAFRP.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of CAFRP may be produced using methods which are generally known in the art. In particular, purified CAFRP may be used to produce antibodies or to screen libraries of pharmaceutical agents to identify those which specifically bind CAFRP. Antibodies to CAFRP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with CAFRP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to CAFRP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of CAFRP amino acids may be fused with those of another protein, such as KLH, and antibodies to the chimeric molecule may be produced.

Monoclonal antibodies to CAFRP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce CAFRP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for CAFRP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CAFRP and its specific antibody. A two-site, monoclonal-based immunoassay utilizing monoclonal antibodies reactive to two non-interfering CAFRP epitopes is preferred, but a competitive binding assay may also be employed. (Maddox, supra.)

In another embodiment of the invention, the polynucleotides encoding CAFRP, or any fragment or complement thereof, may be used for therapeutic purposes. In one aspect, the complement of the polynucleotide encoding CAFRP may be used in situations in which it would be desirable to block the transcription of the mRNA. In particular, cells may be transformed with sequences complementary to polynucleotides encoding CAFRP. Thus, complementary molecules or fragments may be used to modulate CAFRP activity, or to achieve regulation of gene function. Such technology is now well known in the art, and sense or antisense oligonucleotides or larger fragments can be designed from various locations along the coding or control regions of sequences encoding CAFRP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding CAFRP. (See, e.g., Sambrook, supra; and Ausubel, supra.)

Genes encoding CAFRP can be turned off by transforming a cell or tissue with expression vectors which express high levels of a polynucleotide, or fragment thereof, encoding CAFRP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding CAFRP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding CAFRP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding CAFRP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of CAFRP, antibodies to CAFRP, and mimetics, agonists, antagonists, or inhibitors of CAFRP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following:1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of CAFRP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example CAFRP or fragments thereof, antibodies of CAFRP, and agonists, antagonists or inhibitors of CAFRP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, which can be expressed as the LD50/ED50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect.

Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind CAFRP may be used for the diagnosis of disorders characterized by expression of CAFRP, or in assays to monitor patients being treated with CAFRP or agonists, antagonists, or inhibitors of CAFRP. Antibodies useful for diagnostic purposes may be prepared in the same manner as described above for therapeutics. Diagnostic assays for CAFRP include methods which utilize the antibody and a label to detect CAFRP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring CAFRP, including ELISAs, RIAs, and FACS, are known in the art and provide a basis for diagnosing altered or abnormal levels of CAFRP expression. Normal or standard values for CAFRP expression are established by combining body fluids or cell extracts taken from normal mammalian subjects, preferably human, with antibody to CAFRP under conditions suitable for complex formation. The amount of standard complex formation may be quantitated by various methods, preferably by photometric means. Quantities of CAFRP expressed in subject, control, and disease samples from biopsied tissues are compared with the standard values. Deviation between standard and subject values establishes the parameters for diagnosing disease.

In another embodiment of the invention, the polynucleotides encoding CAFRP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of CAFRP may be correlated with disease. The diagnostic assay may be used to determine absence, presence, and excess expression of CAFRP, and to monitor regulation of CAFRP levels during therapeutic intervention.

In one aspect, hybridization with PCR probes which are capable of detecting polynucleotide sequences, including genomic sequences, encoding CAFRP or closely related molecules may be used to identify nucleic acid sequences which encode CAFRP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding CAFRP, alleles, or related sequences.

Probes may also be used for the detection of related sequences, and should preferably have at least 50% sequence identity to any of the CAFRP encoding sequences. The hybridization probes of the subject invention may be DNA or RNA and may be derived from the sequence of SEQ ID NO:2 or from genomic sequences including promoters, enhancers, and introns of the CAFRP gene.

Means for producing specific hybridization probes for DNAs encoding CAFRP include the cloning of polynucleotide sequences encoding CAFRP or CAFRP derivatives into vectors for the production of MRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding CAFRP may be used for the diagnosis of a disorder associated with expression of CAFRP. Examples of such a disorder include, but are not limited to disorders associated with cell proliferation, e.g., arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and disorders associated with inflammation, e.g., AIDS, Addison's disease, adult respiratory distress syndrome, allergies, ankylosing spondylitis, amyloidosis, anemia, asthma, atherosclerosis, autoimmune hemolytic anemia, autoimmune thyroiditis ,bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

The polynucleotide sequences encoding CAFRP may be used in Southern or northern analysis, dot blot, or other membrane-based technologies; in PCR technologies; in dipstick, pin, and ELISA assays; and in microarrays utilizing fluids or tissues from patients to detect altered CAFRP expression. Such qualitative or quantitative methods are well known in the art.

In a particular aspect, the nucleotide sequences encoding CAFRP may be useful in assays that detect the presence of associated disorders, particularly those mentioned above. The nucleotide sequences encoding CAFRP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding CAFRP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of CAFRP, a normal or standard profile for expression is established. This may be accomplished by combining body fluids or cell extracts taken from normal subjects, either animal or human, with a sequence, or a fragment thereof, encoding CAFRP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding CAFRP may involve the use of PCR. These oligomers may be chemically synthesized, generated enzymatically, or produced in vitro. Oligomers will preferably contain a fragment of a polynucleotide encoding CAFRP, or a fragment of a polynucleotide complementary to the polynucleotide encoding CAFRP, and will be employed under optimized conditions for identification of a specific gene or condition. Oligomers may also be employed under less stringent conditions for detection or quantitation of closely related DNA or RNA sequences.

Methods which may also be used to quantitate the expression of CAFRP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Chee et al. (1995) PCT application WO95/11995; Fodor, S. P. A. et al. (1995) U.S. Pat. No. 5,424,186; Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Lockhart, D. J. et al. (1996) Nat. Biotech. 14:1675–1680; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding CAFRP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B.J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology,* VCH Publishers New York, N.Y., pp. 965–968.) Examples of genetic map data can be found in various scientific journals or at the Online Mendelian Inheritance in Man (OMIM) site. Correlation between the location of the gene encoding CAFRP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, CAFRP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between CAFRP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with CAFRP, or fragments thereof, and washed. Bound CAFRP is then detected by methods well known in the art. Purified CAFRP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding CAFRP specifically compete with a test compound for binding CAFRP. In this manner, antibodies can be used to detect the presence of any peptide which shares one or more antigenic determinants with CAFRP.

In additional embodiments, the nucleotide sequences which encode CAFRP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. PROSTNOT16 cDNA Library Construction

The PROSTNOT 16 cDNA library was constructed from prostate tissue obtained from a 68-year-old male. The prostate tissue was excised during a radical prostatectomy along with prostate tissue for which the pathology report indicated was associated with a Gleason grade 3+4 adenocarcinoma which perforated the capsule to involve periprostatic tissue. Surgical margins (distal urethra, right and left bladder bases, right and left apices) were negative for tumor. Initially, the patient presented with elevated prostate specific antigen (PSA) after which he was diagnosed with a malignant neoplasm of the prostate and myasthenia gravis. The patient history included benign hypertension, cerebrovascular disease, arteriosclerotic coronary artery disease, osteoarthritis, type II diabetes without complications, acute myocardial infarction, and alcohol use. The patient's family history included benign hypertension, an episode of acute myocardial infarction, and hyperlipidemia in the patient's mother, and arteriosclerotic coronary artery disease and an episode of acute myocardial infarction in the patient's sibling. The frozen tissues were homogenized and lysed using a POLYTRON PT-3000 Homogenizer (Brinkmann Instruments, Westbury, N.J.) in guanidinium isothiocyanate solution. The lysates were centrifuged over a 5.7 M CsCl cushion using an SW28 rotor in an L8–70M ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated using the OLIGOTEX kit (QIAGEN, Inc., Chatsworth, Calif.) and used to construct the cDNA libraries.

The mRNAs were handled according to the recommended protocols in the SUPERSCRIPT plasmid System for cDNA synthesis and plasmid cloning (Cat. #18248-013, Gibco/BRL). The commercial plasmid PSPORT1 (Gibco/BRL) was digested with Eco RI restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, E. coli strain JM 109. An intermediate plasmid produced by the bacteria failed to digest with Eco RI confirming the desired loss of the Eco RI restriction site.

II. Isolation and Sequencing of cDNA Clones

Plasmid DNA was released from the cells and purified using the R.E.A.L. PREP 96 plasmid kit (Catalog #26173, QIAGEN, Inc.). The recommended protocol was employed except for the following changes:1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from M J Research, Watertown, Mass.) and Applied Biosystems 377 DNA sequencing systems; and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIWESEQ™ database (Incyte Pharmaceuticals). This analysis is much faster than multiple membrane-based hybridizations. In addition, the sensitivity of the computer search can be modified to determine whether any particular match is categorized as exact or homologous The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding CAFRP occurs. Abundance and percent abundance are also reported. Abundance directly reflects the number of times a particular transcript is represented in a cDNA library, and percent abundance is abundance divided by the total number of sequences examined in the cDNA library.

V. Extension of CAFRP Encoding Polynucleotides

The nucleic acid sequence of Incyte Clone 2229466 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier PTC200 thermal cycler; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 al of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2x Carb. The following day, several colonies were randomly picked from each plate and cultured in 150 µl of liquid LB/2x Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [γ-$^{32}$P] adenosine triphosphate (Amersham, Chicago, Ill.), and T4 polynucleotide kinase (DuPont NEN, Boston, Mass.). The labeled oligonucleotides are substantially purified using a SEPHADEX G-25 superfine resin column (Pharmacia & Upjohn, Kalamazoo, Mich.). An aliquot containing 10$^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN, Boston, Mass.).

The DNA from each digest is fractionated on a 0.7 percent agarose gel and transferred to nylon membranes (NYTRAN Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots hybridization patterns are compared visually.

VII. Microarrays

To produce oligonucleotides for a microarray, one of the nucleotide sequences of the present invention is examined using a computer algorithm which starts at the 3' end of the nucleotide sequence. For each, the algorithm identifies oligomers of defined length that are unique to the nucleic acid sequence, have a GC content within a range suitable for hybridization, and lack secondary structure that would interfere with hybridization. The algorithm identifies approximately 20 oligonucleotides corresponding to each nucleic acid sequence. For each sequence-specific oligonucleotide, a pair of oligonucleotides is synthesized in which the first oligonucleotides differs from the second oligonucleotide by one nucleotide in the center of the sequence. The oligonucleotide pairs can be arranged on a substrate, e.g. a silicon chip, using a light-directed chemical process. (See, e.g., Chee, supra.)

Probe sequences may be selected by screening a large number of clones from a variety of cDNA libraries in order to find sequences with conserved protein motifs common to genes coding for signal sequence containing polypeptides. In one embodiment, sequences identified from cDNA libraries, are analyzed to identify those gene sequences with conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify functional or structural domains that cannot be detected using conserved motifs due to extreme sequence divergence. The method is based on weight matrices. Motifs identified by this method are then calibrated against the SWISS-PROT database in order to obtain a measure of the chance distribution of the matches.

In another embodiment, Hidden Markov models (HMMs) may be used to find shared motifs, specifically consensus sequences. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

In the alternative, a chemical coupling procedure and an ink jet device can be used to synthesize oligomers on the surface of a substrate. (See, e.g., Baldeschweiler, supra.) An array analogous to a dot or slot blot may also be used to arrange and link fragments or oligonucleotides to the surface of a substrate using or thermal, UV, mechanical, or chemical bonding procedures, or a vacuum system. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each oligonucleotide sequence on the microarray may be assessed through analysis of the scanned images.

In another alternative, full-length cDNAs or Expressed Sequence Tags (ESTs) comprise the elements of the microarray. Full-length cDNAs or ESTs corresponding to one of the nucleotide sequences of the present invention, or selected at random from a cDNA library relevant to the present invention, are arranged on an appropriate substrate, e.g., a glass slide. The cDNA is fixed to the slide using, e.g., U.V. cross-linking followed, by thermal and chemical and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the CAFRP-encoding sequences, or any parts thereof, are used to detect, decrease, or inhibit expression of naturally occurring CAFRP. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of CAFRP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the CAFRP-encoding transcript.

IX. Expression of CAFRP

Expression of CAFRP is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of CAFRP into bacterial growth media which can be used directly in the following assay for activity.

X. Demonstration of CAFRP Activity

CAFRP activity is measured by its ability to stimulate transcription of a reporter gene, essentially as described in Liu et al (supra). The assay entails the use of a well characterized reporter gene construct, LexA$_{op}$-LacZ, that consists of LexA DNA transcriptional control elements (LexA$_{op}$) fused to sequences encoding the *E. coli* LacZ enzyme. The methods for contructing and expressing fusions genes, introducing them into cells, and measuring LacZ enzyme activity, are well known to those skilled in the art. Sequences encoding CAFRP are cloned into a plasmid that directs the synthesis of a fusion protein, LexA-CAFRP, consisting of CAFRP and a DNA binding domain derived from the LexA transcription factor. The resulting plasmid, encoding a LexA-CAFRP fusion protein, is introduced into yeast cells along with a plasmid containing the LexA$_{op}$-LacZ reporter gene. The amount of LacZ enzyme activity associated with LexA-CAFRP transfected cells, relative to control cells, is proportional to the amount of transcription stimulated by the CAFRP gene sequences.

XI. Production of CAFRP Specific Antibodies

CAFRP substantially purified using PAGE electrophoresis (see, e.g., Harrington, M. G. (1990) Methods Enzymol. 182:488–495), or other purification techniques, is used to immunize rabbits and to produce antibodies using standard protocols. The CAFRP amino acid sequence is analyzed using DNASTAR software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel et al. pra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring CAFRP Using Specific Antibodies

Naturally occurring or recombinant CAFRP is substantially purified by immunoaffinity chromatography using antibodies specific for CAFRP. An immunoaffinity column is constructed by covalently coupling anti-CAFRP antibody to an activated chromatographic resin, such as CNBr-activated SEPHAROSE (Pharmacia & Upjohn). After the coupling, the resin is blocked and washed according to the manufacturer's instructions.

Media containing CAFRP are passed over the immunoaffinity column, and the column is washed under conditions that allow the preferential absorbance of CAFRP (e.g., high ionic strength buffers in the presence of detergent). The column is eluted under conditions that disrupt antibody/CAFRP binding (e.g., a buffer of pH 2 to pH 3, or a high concentration of a chaotrope, such as urea or thiocyanate ion), and CAFRP is collected.

XIII. Identification of Molecules Which Interact with CAFRP

CAFRP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled CAFRP, washed, and any wells with labeled CAFRP complex are assayed. Data obtained using different concentrations of CAFRP are used to calculate values for the number, affinity, and association of CAFRP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO:1.

2. A composition comprising the polynucleotide of claim 1.

3. An isolated and purified polynucleotide which is completely complementary to the polynucleotide of claim 1.

4. An expression vector containing the polynucleotide of claim 1.

5. A method for detecting a polynucleotide encoding a polypeptide comprising the amino acid sequence of SEQ ID NO:1 in a biological sample containing nucleic acids, the method comprising the steps of:
   (a) hybridizing the polynucleotide of claim 3 to at least one of the nucleic acids of the biological sample, thereby forming a hybridization complex;
   (b) washing the hybridization complex under stringent wash conditions of 0.1× saline sodium citrate and 0.5% sodium dodecyl sulfate; and
   (c) detecting the hybridization complex, wherein the presence of the hybridization complex correlates with the presence of a polynucleotide encoding the polypeptide in the biological sample.

6. A host cell containing the expression vector of claim 4.

7. The method of claim 5 wherein the nucleic acids of the biological sample are amplified by the polymerase chain reaction prior to the hybridizing step.

8. A method for producing a polypeptide comprising a sequence of SEQ ID NO:1, the method comprising the steps of:
   (a) culturing the host cell of claim 6 under conditions suitable for the expression of the polypeptide; and
   (b) recovering the polypeptide from the host cell culture.

9. An isolated and purified polynucleotide comprising the polynucleotide sequence of SEQ ID NO:2.

10. An isolated and purified polynucleotide having a sequence completely complementary to the polynucleotide of claim 9.

11. A fragment of the polynucleotide of claim 9 comprising nucleotides 1083 to 1113 of SEQ ID NO:2.

* * * * *

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 292 amino acids
        (B) TYPE: amino acid
        (C) STRANDEDNESS: single
        (D) TOPOLOGY: linear (vii) IMMEDIATE SOURCE:
        (A) LIBRARY: PROSNOT16
        (B) CLONE: 2229466

(xi) SEQUENCE DESCRIPTION: SEQ ID NO:1:

Met Pro Ala Ala Leu Val Glu Asn Ser Gln Val Ile Cys Glu Val Trp
 1               5                  10                  15
```

```
Ala Ser Asn Leu Glu Glu Met Arg Lys Ile Arg Glu Ile Val Leu
         20                  25                  30
Ser Tyr Ser Tyr Ile Ala Met Asp Thr Glu Phe Pro Gly Val Val
         35                  40                  45
Arg Pro Ile Gly Glu Phe Arg Ser Ser Ile Asp Tyr Gln Tyr Gln Leu
 50                  55                  60
Leu Arg Cys Asn Val Asp Leu Leu Lys Ile Ile Gln Leu Gly Leu Thr
 65                  70                  75                  80
Phe Thr Asn Glu Lys Gly Glu Tyr Pro Ser Gly Ile Asn Thr Trp Gln
             85                  90                  95
Phe Asn Phe Lys Phe Asn Leu Thr Glu Asp Met Tyr Ser Gln Asp Ser
             100                 105                 110
Ile Asp Leu Leu Ala Asn Ser Gly Leu Gln Phe Gln Lys His Glu Glu
             115                 120                 125
Glu Gly Ile Asp Thr Leu His Phe Ala Glu Leu Leu Met Thr Ser Gly
         130                 135                 140
Val Val Leu Cys Asp Asn Val Lys Trp Leu Ser Phe His Ser Gly Tyr
145                 150                 155                 160
Asp Phe Gly Tyr Met Val Lys Leu Leu Thr Asp Ser Arg Leu Pro Glu
                 165                 170                 175
Glu Glu His Glu Phe Phe His Ile Leu Asn Leu Phe Phe Pro Ser Ile
             180                 185                 190
Tyr Asp Val Lys Tyr Leu Met Lys Ser Cys Lys Asn Leu Lys Gly Gly
             195                 200                 205
Leu Gln Glu Val Ala Asp Gln Leu Asp Leu Gln Arg Ile Gly Arg Gln
         210                 215                 220
His Gln Ala Gly Ser Asp Ser Leu Leu Thr Gly Met Ala Phe Phe Arg
225                 230                 235                 240
Met Lys Glu Leu Phe Phe Glu Asp Ser Ile Asp Asp Ala Lys Tyr Cys
                 245                 250                 255
Gly Arg Leu Tyr Gly Leu Gly Thr Gly Val Ala Gln Lys Gln Asn Glu
             260                 265                 270
Asp Val Asp Ser Ala Gln Glu Lys Met Ser Ile Leu Ala Ile Ile Asn
         275                 280                 285
Asn Met Gln Gln
         290

(2) INFORMATION FOR SEQ ID NO:2:

(i) SEQUENCE CHARACTERISTICS:
        (A) LENGTH: 2852 base pairs
        (B) TYPE: nucleic acid
        (C) STRANDEDNESS: single
        (D) TOPOLOGY: linear (vii) IMMEDIATE SOURCE:
        (A) LIBRARY: PROSNOT16
        (B) CLONE: 2229466

(xi) SEQUENCE DESCRIPTION: SEQ ID NO:2:

CCGTGGGAGG CACGTAAGAC CGCTCTGGGC ACGGGGCGC TCACCTCACT GGCTCGTTCG    60

GTTCTAGGAG CAGATCCGGG GTAGAGGGAA AAGAGCTCCG GGCCAGGGGC TGCCGTCGCC   120

GCCGTCGGGG AGTCAGCCCG CCAGCCCGCC AGCTCGTCAG CCCGCCAGCC AGCGCTTCGC   180

GGGCCCTGTC GGTCCCGATC AGACCAAACA TTGTCTGGCT TGCACTGTAA AACTAGTTAG   240

CTGAAGACGA CTTCTCAGGT TTCTTCAGGA TGCCTGCAGC ACTTGTGGAG AATAGCCAGG   300

TTATCTGTGA AGTGTGGGCC AGTAATCTAG AAGAAGAGAT GAGGAAGATC CGAGAAATCG   360
```

```
TGCTCAGTTA CAGTTATATT GCCATGGACA CAGAATTTCC AGGTGTTGTG GTGCGACCAA    420

TTGGTGAATT TCGTAGTTCC ATAGATTACC AATATCAGCT TCTGCGGTGC AATGTTGACC    480

TTTTAAAAAT TATCCAGCTG GGCCTTACAT TCACAAATGA GAAGGGAGAG TATCCTTCTG    540

GAATCAATAC TTGGCAGTTC AATTTCAAAT TTAACCTTAC AGAGGACATG TACTCCCAGG    600

ATTCCATAGA TCTCCTTGCT AACTCAGGAC TACAGTTTCA GAAGCATGAA GAGGAAGGGA    660

TTGACACACT GCACTTTGCA GAGCTGCTTA TGACATCAGG AGTGGTTCTC TGTGACAATG    720

TCAAATGGCT TTCATTTCAT AGTGGCTATG ATTTTGGCTA TATGGTAAAG TTGCTTACAG    780

ATTCTCGTTT GCCAGAAGAG GAACATGAAT TCTTTCATAT TCTGAACCTT TTCTTCCCAT    840

CCATTTATGA TGTGAAATAC CTGATGAAGA GCTGCAAAAA TCTTAAGGGA GGTCTTCAGG    900

AAGTTGCTGA TCAGTTGGAT TTGCAGAGGA TTGGAAGGCA GCACCAGGCA GGCTCAGACT    960

CACTGCTGAC AGGAATGGCT TTCTTTAGGA TGAAAGAGTT GTTTTTTGAG GACAGCATTG   1020

ATGATGCCAA GTACTGTGGG CGGCTCTATG GCTTAGGCAC AGGAGTGGCC CAGAAGCAGA   1080

ATGAGGATGT GGACTCTGCC CAGGAGAAGA TGAGCATCCT GGCGATTATC AACAACATGC   1140

AGCAGTGATG GCGCCAGGCT CTGCAGGGTG GGCCTGATCC CAGAGTGGTG CTTACTGTGC   1200

TGACTGTGTA CTTATCTTCC CCAAGAGAAA ATGCTTCTTT TGAGCACACT GTACCTACCA   1260

TCTGCATTGA GCAGAAAGAC TTTTGTTTTA CTGAAGACAA AGATGTTTT TATTTTAGAC    1320

CCAGAAGAGA GGAGTTTGCT CTGAATTTGT AAATAAGTCT TCCCCATTCC TCATACTGA    1380

GCCTCTCCTC TCTGGTTGCC TCCTGCCACC AGCATCCATG GCTCATTTGA CACCTTTTA    1440

AATATCAGGA CAAGTCTGAA ACAAAGTAGT AAAATGTATA TAACTCTTAC CTGTTGTCAT   1500

TCTTTTTCTT TTAAATTTGT TGCTAATCTC TGATAATGAA GATTCTTACT CTGATTCTCA   1560

GCTGAGCTGT GAGGGCTTCC AGGGAAAATG GAACAAAATG GTGTTCTTAG GTAATGGGTT   1620

GTAGATACTG AGTCTTCCTT TCCTTTTCTG ACCCTTCTCG AGGACATTTG CTTTCCTCAC   1680

ACTTTTGTAG TCTCTCTTTA CATATTACTA TATGGAAATG AATTGCTCTG TGCTGAAATT   1740

TGAAGACCAG ATAATGAAAC TGAAAAGCAA ACAATTTTAC TGAATCTGTC TACCCTTCAT   1800

TCATGAGAAC TCCAGAATGA GTGTTGACCA CTGAAGCATC TTTTAAGTCT GTGTTCCATT   1860

GTGCCATTCA GGTTTGCTGT CACATATGCA TCATCTGAAA TCATTTGAAA TTTTTGTACA   1920

ATAAAATATC CTGGATTTGA TCCTGAAGGA AACTAGTAAG ATCAGATTTT TGGGTCATGT   1980

CTGTTGTATT TTCAGTAATG TGATTTCAGA TGGTCATCTG GATTCTCCCA CTTCTCTACT   2040

CCATTATTTC TCTACTTTTC CTTCCAGCAA ACCTGAAACG TGAGGGAGAT GGATTAATGT   2100

GAGTAACAGG AATGTGTCTT TAAAAAGCTA GAGTGGTTAC ATTTAATCAG GCAGTAAGAT   2160

AATTTGGGTT CTTGAGTTGT TTTGGAGTAA TATCCCACAA CTGGGGTAGG AAGCTCAGGA   2220

CTTTTTTCTT TAAAGCTAGT CATTTCAAAA GCATATTGTA TTTTTTTGAA TGCTACAGT    2280

ATGGACAATT TCAAAAACCA AAACCCACTT TGGATTGGTG GAAGTAAAAA CTGGTAACTC   2340

ACTCAAGTGA ATGAATGGTC TTGCATTTTA AAAGCTTATG GGAAACTCAA TTTGAAATGA   2400

TTAGAAAATG TCAAGTATTA TAAGCTGGTA TTTAAGATGC TTGTAAATAC TATTTATGTT   2460

TTTAATTTTG TAAAATAAAG ATTTCTTTTT AACCACTGGC AAAAAAAAAA AAAAAAAAA    2520

AAAAAAAAAA AAAAAAAAAA AAAAAAAAAA AAAAAAAAAA AAAAAAAAAA AAAAAAAAA    2580

AAAAAAGGGG GGGCCGCTCT AGGGGTCCCA GGTTTAGGTA CGGGGGCTTG GGGGGTCAAG   2640

CCCCTCCTAA GGGGCCCCCA AATTTCATTT CCCGGGCGGC GGTTTTAAAA GGTCGTGCCG   2700

GGGAAACCCC GGGGGTTCCC CACTTTAACC GCTTTGGGGA AATCCCCCTT TTGGCAAGTG   2760
```

```
GGGGTATTAG GGAAGGGGCC CGCCCGGTTG GCCTTTCCCA AAGTTTGCGC CCTCTAATTG    2820

GGCATTGGGC CGCCCCCTTT AGGGGCGCTT TA                                  2852

(2) INFORMATION FOR SEQ ID NO:3:

(i) SEQUENCE CHARACTERISTICS:
        (A) LENGTH: 285 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 726136

(xi) SEQUENCE DESCRIPTION: SEQ ID NO:3:

Met Pro Ala Ala Thr Val Asp His Ser Gln Arg Ile Cys Glu Val Trp
1               5                   10                  15

Ala Cys Asn Leu Asp Glu Glu Met Lys Lys Ile Arg Gln Val Ile Arg
                20                  25                  30

Lys Tyr Asn Tyr Val Ala Met Asp Thr Glu Phe Pro Gly Val Val Ala
            35                  40                  45

Arg Pro Ile Gly Glu Phe Arg Ser Asn Ala Asp Tyr Gln Tyr Gln Leu
        50                  55                  60

Leu Arg Cys Asn Val Asp Leu Leu Lys Ile Ile Gln Leu Gly Leu Thr
65                  70                  75                  80

Phe Met Asn Glu Gln Gly Glu Tyr Pro Pro Gly Thr Ser Thr Trp Gln
                85                  90                  95

Phe Asn Phe Lys Phe Asn Leu Thr Glu Asp Met Tyr Ala Gln Asp Ser
                100                 105                 110

Ile Glu Leu Leu Thr Thr Ser Gly Ile Gln Phe Lys Lys His Glu Glu
            115                 120                 125

Glu Gly Ile Glu Thr Gln Tyr Phe Ala Glu Leu Leu Met Thr Ser Gly
        130                 135                 140

Val Val Leu Cys Glu Gly Val Lys Trp Leu Ser Phe His Ser Gly Tyr
145                 150                 155                 160

Asp Phe Gly Tyr Leu Ile Lys Ile Leu Thr Asn Ser Asn Leu Pro Glu
                165                 170                 175

Glu Glu Leu Asp Phe Phe Glu Ile Leu Arg Leu Phe Phe Pro Val Ile
                180                 185                 190

Tyr Asp Val Lys Tyr Leu Met Lys Ser Cys Lys Asn Leu Lys Gly Gly
            195                 200                 205

Leu Gln Glu Val Ala Glu Gln Leu Glu Leu Glu Arg Ile Gly Pro Gln
        210                 215                 220

His Gln Ala Gly Ser Asp Ser Leu Leu Thr Gly Met Ala Phe Phe Lys
225                 230                 235                 240

Met Arg Glu Met Phe Phe Glu Asp His Ile Asp Asp Ala Lys Tyr Cys
                245                 250                 255

Gly His Leu Tyr Gly Leu Gly Ser Gly Ser Ser Tyr Val Gln Asn Gly
                260                 265                 270

Thr Gly Asn Ala Tyr Glu Glu Glu Ala Ser Lys Gln Ser
            275                 280                 285
```